US005518187A

United States Patent [19]
Bruno et al.

[11] Patent Number: 5,518,187
[45] Date of Patent: May 21, 1996

[54] METHOD OF GRINDING PHARMACEUTICAL SUBSTANCES

[75] Inventors: Joseph A. Bruno, Blue Bell; Brian D. Doty, Phoenixville; Evan Gustow, Ardmore; Kathleen J. Illig; Nats Rajagopalan, both of Phoenixville; Pramod Sarpotdar, Malvern, all of Pa.

[73] Assignee: Nano Systems L.L.C., Collegeville, Pa.

[21] Appl. No.: 180,827

[22] Filed: Jan. 12, 1994

Related U.S. Application Data

[63] Continuation of Ser. No. 981,639, Nov. 25, 1992, abandoned.
[51] Int. Cl.$^6$ .......................... B02C 17/20; B02C 23/18
[52] U.S. Cl. ................... 241/5; 241/21; 241/22; 241/170; 241/184
[58] Field of Search .................... 241/5, 21, 22, 241/30, 170–184; 424/63, 165.1, 489

[56] References Cited

U.S. PATENT DOCUMENTS

| 1,807,383 | 5/1931 | Carnahan | 241/184 X |
| 3,104,068 | 9/1963 | Castelli et al. | |
| 4,404,346 | 9/1983 | Pirotta | 424/78.12 |
| 4,974,368 | 12/1990 | Miyamoto | 51/124 R |
| 5,066,335 | 11/1991 | Lane | 51/302 |
| 5,066,486 | 11/1991 | Kamen | 424/63 |
| 5,145,684 | 9/1992 | Liversidge | 424/489 |
| 5,320,284 | 6/1994 | Nishida et al. | 241/21 |

FOREIGN PATENT DOCUMENTS

| 247895 | 12/1987 | European Pat. Off. | 241/184 |
| 498482 | 12/1992 | European Pat. Off. | |

Primary Examiner—Timothy V. Eley
Attorney, Agent, or Firm—Rudman & Balogh

[57] ABSTRACT

A method of preparing particles of a drug substance or diagnostic imaging agent which comprises grinding the drug substance or imaging agent in the presence of grinding media comprising a polymeric resin. The method provides particles exhibiting reduced contamination.

16 Claims, No Drawings

METHOD OF GRINDING PHARMACEUTICAL SUBSTANCES

This is a continuation of application Ser. No. 07/981,639 filed on Nov. 25, 1992 now abandoned.

BACKGROUND OF THE INVENTION

Inasmuch as the rate of dissolution of a particle can increase with increasing surface area, i.e., decreasing particle size, efforts have been made to control the size and size range of drug particles in pharmaceutical compositions by a variety of methods, including various milling techniques, such as airjet milling and wet milling. However, there tends to be a bias in the pharmaceutical arts against milling techniques, particularly, wet milling, due to concerns associated with contamination. For example, in the preparation of pharmaceuticals for oral and parenteral applications, it is desirable to have total contamination, e.g., of heavy metals, below about 10 parts per million. The need to control and minimize contamination is particularly critical in the milling of parenteral products due to potential safety issues associated with injection of contaminants.

Various grinding media, such as stainless steel, zirconium silicate, zirconium oxide, glass, and the like, typically in the form of spherical beads, are commonly used in various mills, including media mills, for grinding materials. However, the use of stainless steel media can result in the introduction of iron, chromium and/or nickel contamination to the milled product accompanied by product discoloration. Media fabricated of conventional materials, such as zirconium silicates and zirconium oxides often contain zirconium, silicon, barium, lead, hafnium, yttrium, thorium and uranium, all of which can enter the product during grinding, leading to potential safety issues. Glass media can contain various alkali oxides, which are an unacceptable source of contamination. Additionally, most commercially available glass media for fine grinding are of the soda lime type, which is not well suited for milling pH sensitive products due to high alkalinity which can result during milling.

Liversidge et al, U.S. Pat. No. 5,145,684, and EPO 498,492, describe dispersible particles consisting of a drug substance or an x-ray contrast agent having a surface modifier adsorbed on the surface thereof in an amount sufficient to maintain an effective average particle size of less than about 400 nm. The particles are prepared by dispersing a drug substance or contrast agent in a liquid dispersion medium and wet grinding in the presence of rigid grinding media. Particles free of unacceptable contamination have been prepared in accordance with this method.

Nevertheless, further reduced levels of contamination are desired. This is particularly so when 1) the drug substance or imaging agent is to be ground in a high energy mill where contamination tends to be particularly problematic, and/or 2) the drug substance or imaging agent is intended for parenteral use, in which case the risks associated with contaminated product can be particularly severe.

SUMMARY OF THE INVENTION

We have discovered that fine particles of diagnostic imaging agents and drug substances can be prepared with reduced contamination by milling in the presence of grinding media comprising a polymeric resin.

More specifically, in accordance with this invention, there is provided a method of preparing particles of an organic diagnostic imaging agent or drug substance which comprises grinding the imaging agent or drug substance in the presence of grinding media comprising a polymeric resin. The media can comprise particles consisting essentially of the polymeric resin. Alternatively, the media can comprise particles comprising a core, which preferably is a conventional media material, having adhered thereon a coating of the polymeric resin.

It is a particularly advantageous feature of this invention that there is provided a method of preparing fine particles of a diagnostic imaging agent or a drug substance having reduced contamination and/or discoloration.

Still another advantageous feature of this invention is that there is provided a method of fine grinding drugs and imaging agents, which method generates less heat and reduces potential heat-related problems such as chemical instability and contamination.

It is another advantageous feature of this invention that a method of fine grinding drugs and imaging agents is provided enabling improved pH control.

Other advantageous features will become apparent upon reference to the following Description of Preferred Embodiments.

DESCRIPTION OF PREFERRED EMBODIMENTS

This invention is based partly on the unexpected discovery that imaging agents and drug substances can be prepared in extremely fine particles with reduced contamination levels by grinding in the presence of grinding media comprising a polymeric resin. While this invention is described herein in connection with its preferred utilities, i.e., with respect to drug substances for use in pharmaceutical compositions and imaging agents for use in x-ray contrast compositions, it is also believed to be useful in other applications, such as the grinding of particles for cosmetic and photographic compositions, where contamination can be a concern.

In the method of this invention, a drug substance is prepared in the form of particles by grinding the agent or drug substance in the presence of a grinding media comprising a polymeric resin.

The grinding media can comprise particles, preferably substantially spherical in shape, e.g., beads, consisting essentially of the polymeric resin. Alternatively, the grinding media can comprise particles comprising a core having a coating of the polymeric resin adhered thereon.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to 3.0 g/cm$^3$. Higher density resins are preferred inasmuch as it is believed that these provide more efficient particle size reduction.

The media can range in size from about 0.1 to 3 mm. For fine grinding, the particles preferably are from 0.2 to 2 mm, more preferably, 0.25 to 1 mm in size.

The core material preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials have a density greater than about 2.5 g/cm$^3$. The selection of high density core materials is believed to facilitate efficient particle size reduction.

Useful thicknesses of the polymer coating on the core are believed to range from about 1 to about 500 microns, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like.

The milling process can be a dry process, e.g., a dry roller milling process, or a wet process, i.e., wet-grinding. In preferred embodiments, this invention is practiced in accordance with the wet-grinding process described in U.S. Pat. No. 5,145,684 and EPO 498,482. Thus, the wet grinding process can be practiced in conjunction with a liquid dispersion medium and surface modifier such as described in these publications. Useful liquid dispersion media include water, aqueous salt solutions, ethanol, butanol, hexane, glycol and the like. The surface modifier can be selected from known organic and inorganic pharmaceutical excipients such as described in U.S. Pat. No. 5,145,684 and can be present in an amount of 0.1–90%, preferably 1–80% by weight based on the total weight of the dry particle.

In preferred embodiments, the drug substance or imaging agent can be prepared in submicron or nanoparticulate particle size, e.g., less than about 500 nm. Applicants have demonstrated that particles can be prepared having an average particle size of less than about 400 nm. In certain embodiments, particles having an average particle size of less than 300 nm have been prepared in accordance with the present invention. It was particularly surprising and unexpected that such fine particles could be prepared at such low levels of contamination.

Grinding can take place in any suitable grinding mill. Suitable mills include an airjet mill, a roller mill, a ball mill, an attritor mill, a vibratory mill, a planetary mill, a sand mill and a bead mill. A high energy media mill is preferred when the grinding media consists essentially of the polymeric resin. The mill can contain a rotating shaft.

The preferred proportions of the grinding media, the drug substance and/or imaging agent, the optional liquid dispersion medium, and surface modifier present in the grinding vessel can vary within wide limits and depends, for example, upon the particular drug substance or imaging agent selected, the size and density of the grinding media, the type of mill selected, etc. The process can be carried out in a continuous, batch or semi-batch mode. In high energy media mills, it can be desirable to fill 70–90% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium.

The attrition time can vary widely and depends primarily upon the particular drug substance or imaging agent, mechanical means and residence conditions selected, the initial and desired final particle size and so forth. For roller mills, processing times from several days to weeks may be required. On the other hand, residence times of less than about 8 hours are generally required using high energy media mills.

After attrition is completed, the grinding media is separated from the milled particulate product (in either a dry or liquid dispersion form) using conventional separation techniques, such as by filtration, sieving through a mesh screen, and the like.

The invention can be practiced with a wide variety of drug substances and diagnostic imaging agents. In the case of dry milling, the drug substances and imaging agents must be capable of being formed into solid particles. In the case of wet milling, the drug substances and imaging agents must be poorly soluble and dispersible in at least one liquid medium. By "poorly soluble", it is meant that the drug substance or imaging agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media.

Suitable drug substances and classes of drug substances are described in U.S. Pat. No. 5,145,684 and include Danazol, 5α, 17α,-1'-(methylsulfonyl)-1'H-pregn-20-yno[3,2-c]-pyrazol-17-ol, camptothecin, piposulfam, piposulfan and naproxen. Other suitable drug substances include the NSAIDs described in U.S. patent application Ser. No. 897,193 filed Jun. 10, 1992, and the anticancer agents described in U.S. patent application Ser. No. 908,125 filed Jul. 1, 1992, the disclosures of which are hereby incorporated by reference.

Suitable diagnostic imaging agents include ethyl-3,5-bisacetoamido- 2,4,6-triiodobenzoate (WIN 8883), ethyl (3,5-bis(acetylamino)- 2,4,6-triodobenzoyloxy) acetate (WIN 12901), ethyl- 2-(bis (acetylamino)-2,4,6-triiodobenzoyloxy)butyrate (WIN 16318), 6-ethoxy- 6-oxohexyl-3,5-bis(acetylamino)-2,4,6-triiodobenzoate (WIN 67722). Other suitable imaging agents are described in EPO 498,482.

The following examples further illustrate the invention.

EXAMPLE 1

Preparation of WIN 8883 Particles Using Polycarbonate Beads as the Grinding Media A dispersion (500 ml) was prepared by combining 30% w/v WIN 8883 (150 g), 7% Tetronic™-908 (35 g), which is a tetrafunctional block copolymer derived from sequential addition of propylene oxide and ethylene oxide to ethylenediamine, available from BASF, and water. Polycarbonate beads (250 ml, average particle size 0.3 mm) were added to the grinding chamber (300 ml, grade 316 stainless steel) of a Dyno-Mill (Model KDL, manufactured by Willy A. Bachoffen AG Maschinfabrik). The dispersion was recirculated through the mill using a positive displacement pump at a flow rate of 150 ml/min. The residence time of the dispersion in the milling chamber was 60 min. The shaft in the grinding chamber jacket was rotated at 4200 RPM (tip speed 14 m/sec). The temperature of the chamber jacket was controlled to below about 30° C. with a recirculating ice water bath. The dynamic gap separator was adjusted to a gap thickness of about 0.1 mm, such that the grinding media was retained within the chamber while the dispersion was recirculated. The resulting particles (average particle size, 200 nm) had no noticeable discoloration, indicating minimal attrition of stainless steel into the product. When a similar procedure was carried out using grinding media fabricated of zirconium silicate on glass beads, the resulting product exhibited noticeable discoloration.

EXAMPLES 2–4

Preparation of WIN 8883 Particles Using Polystyrene Beads as the Grinding Media

A dispersion (500 ml) was prepared by combining 30% w/v WIN 8883 (150 g), 7% Tetronic™-908 (35 g), and water. Polystyrene beads (250 ml, average particle size 0.5 mm, range 0.3–0.6 mm) were added to the grinding chamber (300 ml) of a DYNO®-MILL. The polystyrene contained divinylbenzene as the crosslinker. The dispersion was recirculated through the mill at a flow rate of 150 ml/min for a calculated residence time of 70 min. The shaft in the grinding chamber was rotated at 4200 RPM, and the temperature of the chamber jacket was controlled to below about 30° C. The resulting product (average particle size 180 nm) exhibited no noticeable discoloration, indicating minimal presence of stainless steel contamination in the product.

In Example 3, a dispersion (500 ml) was prepared by combining 30% (w/v) WIN 8883 (150 g), 7% Tetronic™-908 (35 g), and water. Polystyrene beads (250 ml, average particle size 0.355 mm) were added to the grinding chamber (300 ml) of a DYNO®-MILL. The dispersion was recirculated through the mill at a flow rate of 150 ml/min for a residence time of 70 minutes. The shaft of the grinding chamber was rotated at 3200 RPM, and the temperature of the chamber jacket was controlled to below about 30° C. The resulting product (average particle size 190 nm) exhibited no noticeable discoloration, indicating minimal presence of stainless steel contamination in the product.

In Example 4, the procedure described for Examples 2 and 3 was substantially repeated except that the shaft was rotated at 2500 RPM and the calculated residence time of the dispersion in the chamber was 140 min. The resulting particle size was 200 nm with no noticeable discoloration.

EXAMPLE 5

Measurement of Reduced Contamination by ICP-MS and ICP-AES

A dispersion (500 ml) was prepared by combining 30% (w/v) WIN 8883 (150 g), 7% Tetronic™-908 (35 g), and water. Polycarbonate beads (250 ml, size 0.3 mm–0.5 mm) were added to the grinding chamber (300 ml) of a DYNO®-MILL. The dispersion was recirculated through the mill at a flow rate of 150 ml/min for a residence time of 70 minutes. The shaft of the grinding chamber was rotated at 3200 RPM (tip speed 10.5 m/sec) and the temperature of the chamber jacket was controlled to below about 30° C. The resulting product (average particle size 225 nm) exhibited low levels of contamination (as set forth in the table below) when examined by inductively coupled plasma—mass spectroscopy (ICP-MS) and inductively coupled plasma—atomic emission spectroscopy (ICP-AES).

|  | Contamination (ppm) | | | | | |
| --- | --- | --- | --- | --- | --- | --- |
|  | Zr | Si | Fe | Ba | Cr | Ni |
| Example 4 | 0.7 | 3 | 1 | — | 1 | — |
| Comp. Ex. A | 0.5 | 210 | 12 | 43 | 2 | 2 |
| Comp. Ex. B | 250 | 220 | 17 | — | 4 | 3 |

— Indicates contamination below detection levels.

In Comparative Example A, a similar dispersion was milled to 194 nm using 0.5 mm glass beads. The shaft of the grinding chamber was rotated at 3200 RPM (tip speed 10.5 m/sec). The product exhibited substantially higher levels of silicon, iron, chromium and nickel.

In Comparative Example B, a similar dispersion was milled to 195 nm using 0.75 mm $ZrSiO_2$ beads. The shaft of the grinding chamber was rotated at 3200 RPM (tip speed 10.5 m/sec). The product exhibited substantially higher levels of zirconium, silicon, iron, chromium and nickel.

EXAMPLE 6

Preparation of Nanoparticulate Naproxen Using Polycarbonate Beads in a Planetary Mill Polycarbonate beads (6 ml, average particle size 0.3 mm) were added to a 12 ml agate bowl of a planetary mill (Model #LC-107 Fritsch P-7 Planetary micro mill available from Gilson Inc.). To the bowl was added naproxen (150 mg), Pluronic™F-68 (90 mg), a block copolymer of ethylene oxide and propylene oxide available from BASF, and 2.7 ml water for injection to give a final concentration (w/v) of 5% naproxen and 3% surface modifier. The second agate bowl contained 6 ml media as a counterweight. The dispersion was milled at medium speed (2.5 dial setting on the speed control) for 2.5 days. The naproxen particle size was measured at various time intervals as follows:

| Time | Particle Size (nm) |
| --- | --- |
| 3 hours | 24,200 |
| 18 hours | 316 |
| 36 hours | 288 |
| 60 hours | 348 |

The resulting milky white product had no noticeable discoloration or particulate contaminants.

The invention has been described in detail with particular reference to certain preferred embodiments thereof, but it will be understood that variations and modifications can be effected within the spirit and scope of the invention.

We claim:

1. A method of preparing particles of a diagnostic imaging agent by grinding said agent with rigid grinding media to reduce said particles to submicron size, wherein said grinding media has a substantially spherical shape, has a particle size range of 0.1 to 3 mm and comprises a polymeric resin.

2. The method of claim 1 wherein said grinding media comprises particles containing a core having adhered thereon a coating of said polymeric resin.

3. The method of claim 1 wherein said polymer is polystyrene crosslinked with divinyl benzene.

4. The method of claim 1 wherein said polymer is polycarbonate.

5. The method of claim 1 wherein said method is a wet grinding process.

6. The method of claim 1 wherein said method is a dry grinding process.

7. The method of claim 1 wherein said grinding takes place in a mill selected from an airjet mill, a roller mill, a ball mill, an attritor mill, a vibratory mill, a planetary mill, a sand mill, and a bead mill.

8. The method of claim 1 wherein said imaging agent is WIN 8883.

9. A method of preparing particles of a drug substance by grinding said substance with rigid grinding media to reduce said particles to submicron size, wherein said grinding media has a substantially spherical shape, has a particle size range of 0.1 to 3 mm and comprises a polymeric resin.

10. The method of claim 9 wherein said grinding media comprises particles containing a core having adhered thereon a coating of said polymeric resin.

11. The method of claim 9 wherein said polymer is polystyrene crosslinked with divinyl benzene.

12. The method of claim 9 wherein said polymer is polycarbonate.

13. The method of claim 9 wherein said method is a wet grinding process.

14. The method of claim 9 wherein said method is a dry grinding process.

15. The method of claim 9 wherein said grinding takes place in a mill selected from an airjet mill, a roller mill, a ball mill, an attritor mill, a vibratory mill, a planetary mill, a sand mill, and a bead mill.

16. The method of claim 9 wherein said drug substance is naproxen.

* * * * *